(12) United States Patent
Wang

(10) Patent No.: US 11,331,414 B2
(45) Date of Patent: May 17, 2022

(54) METHOD FOR PREPARING INORGANIC NANOPARTICLE-GELATIN CORE-SHELL COMPOSITE PARTICLES

(71) Applicant: SHENZHEN HUANOVA BIOTECHNOLOGY LTD., Guangdong (CN)

(72) Inventor: Huanan Wang, Liaoning (CN)

(73) Assignee: SHENZHEN HUANOVA BIOTECHNOLOGY LTD., Guangdong (CN)

( * ) Notice: Subject to any disclaimer, the term of this patent is extended or adjusted under 35 U.S.C. 154(b) by 246 days.

(21) Appl. No.: 16/743,796

(22) Filed: Jan. 15, 2020

(65) Prior Publication Data

US 2020/0147270 A1 May 14, 2020
US 2021/0001008 A2 Jan. 7, 2021

Related U.S. Application Data

(63) Continuation-in-part of application No. PCT/CN2018/096245, filed on Jul. 19, 2018.

(30) Foreign Application Priority Data

Jul. 21, 2017 (CN) .......................... 201710600536.0

(51) Int. Cl.
| | | |
|---|---|---|
| A61L 27/48 | (2006.01) | |
| A61L 27/52 | (2006.01) | |
| B82Y 5/00 | (2011.01) | |
| B82Y 30/00 | (2011.01) | |
| B82Y 40/00 | (2011.01) | |

(52) U.S. Cl.
CPC ............ *A61L 27/48* (2013.01); *A61L 27/52* (2013.01); *A61L 2430/02* (2013.01); *B82Y 5/00* (2013.01); *B82Y 30/00* (2013.01); *B82Y 40/00* (2013.01)

(58) Field of Classification Search
CPC ...................................................... A61L 27/52
See application file for complete search history.

(56) References Cited

U.S. PATENT DOCUMENTS

| | | | | |
|---|---|---|---|---|
| 4,965,007 A | * | 10/1990 | Yudelson | B03C 1/01 252/62.53 |
| 5,169,754 A | * | 12/1992 | Siiman | B03C 1/01 427/131 |
| 2006/0051427 A1 | * | 3/2006 | Talton | A61L 27/222 424/549 |
| 2007/0048366 A1 | | 3/2007 | Chen et al. | |
| 2008/0003292 A1 | | 1/2008 | Ahlers et al. | |
| 2010/0233219 A1 | * | 9/2010 | Aimi | A61K 49/1833 424/401 |

FOREIGN PATENT DOCUMENTS

| | | |
|---|---|---|
| CN | 103536964 A | 1/2014 |
| CN | 103841965 A | 6/2014 |
| CN | 104971366 A | 10/2015 |
| CN | 106178129 A | 12/2016 |
| KR | 10-2015-0029335 A | 3/2015 |
| WO | WO 2012/051220 A1 | 4/2012 |
| WO | WO 2017/048120 A1 | 3/2017 |

* cited by examiner

*Primary Examiner* — Kyle A Purdy
(74) *Attorney, Agent, or Firm* — Muncy, Geissler, Olds & Lowe, P.C.

(57) ABSTRACT

The present disclosure provides a method for preparing inorganic nanoparticle-gelatin core-shell composite nanoparticles, comprising: dissolving gelatin in a aqueous solution (in which inorganic nanoparticles are dispersed in) to obtain the gelatin-contained aqueous solution, dropwise adding a polar organic solvent to obtain a suspension of inorganic nanoparticle-gelatin core-shell composite particles of nanometer size or submicrometer size, then adding a cross-linking agent thereto to cross-link the gelatin components of the composite particles, followed by washing step to finally obtain inorganic nanoparticle-gelatin core-shell composite micro/nano-particles with inorganic nanoparticles as the core and gelatin as the shell. The present invention firstly provides a process for preparing the core-shell composite nano-scaled particles with inorganic nanoparticles as the core and gelatin as the shell by using a co-precipitation method which is simple and convenient, and beneficial for applying to industrial mass production.

12 Claims, 12 Drawing Sheets

X-ray energy (KeV)

METHOD FOR PREPARING INORGANIC NANOPARTICLE-GELATIN CORE-SHELL COMPOSITE PARTICLES

CROSS REFERENCE TO RELATED APPLICATIONS

This application is a Continuation-in-Part of co-pending International Application No. PCT/CN2018/096245, filed on Jul. 19, 2018, and for which priority is claimed under 35 U.S.C. § 120; and this application claims priority of Application No. 201710600536.0 filed in China on Jul. 21, 2017 under 35 U.S.C. § 119, the entire contents of all of which are hereby incorporated by reference.

TECHNICAL FIELD

The present invention relates to a method for preparing inorganic nanoparticle-gelatin core-shell composite particles for applications in biomedical engineering field.

BACKGROUND ART

Nanotechnology is a multidisciplinary subject that encompasses many different fields including biomedicine, pharmacy, agriculture, environment, advanced materials, chemistry, physics, electronics, information technology, etc. Particularly in the biomedicine field, the synthesis of nanomaterials with a particle size of around 100 nm, and studies and medical applications thereof have become a research focus in recent years. For example, these nanomaterials can be used as medical imaging agents, drug sustained release carriers and diagnostic tools, etc. The studies of nanomaterials in the biomedicine field become popular because the nanotechnology links the engineering with biology and traditional medicines and enables their applications in biomedical fields, including clinical diagnosis, disease monitoring, nanotechnology treatment, bioimaging and genetic manipulation, etc. Although a large number of new nanomaterials are being developed continuously, one of the critical problems is the surface modification and processing of nanomaterials, especially for applications in biological applications such as drug delivery, therapeutic applications and diagnostic auxiliaries.

Although nanomaterials have many uses and advantages, they are often cytotoxic because they can easily penetrate the cell membranes to enter the organisms and interfere with the basal metabolic processes in the cells. Nanoparticles can easily enter the whole body through the circulatory system and even enter the neural network (through nerve cells). The concentration of nanoparticles in human body cannot be effectively reduced by phagocytosis of macrophages and detoxification in the liver and spleens, which may eventually cause incurable diseases such as Alzheimer's disease and Parkinson's disease, etc. In addition to the toxicity, nanoparticles are prone to accumulate in the body since they cannot be eliminated by matrix metabolism in the human body. The accumulated nanomaterials may evenly lead to serious diseases.

The emergence of nanoparticles with a core-shell structure using a material as core and another material as shell provides a feasible solution to address the cytotoxicity of nanomaterials. In the biomedical applications, core-shell nanoparticles have more advantages than simple single-phase nanoparticles, for example, the core-shell nanoparticles have less cytotoxicity, better dispersibility, biocompatibility and cell compatibility, and can bind to bioactive molecules better, and have higher thermal and chemical stability, etc. In details, first, when the required nanoparticles are toxic and may cause pathological changes in the host tissues and organs, the coating of toxic nanoparticles using a biocompatible material can solve the problems of toxicity and biological compatibility. This shell material can act as a non-toxic layer and improve the performance of core material. Second, the hydrophilicity of nanoparticles is very important for their application in biological systems. The core-shell nanoparticle with a hydrophilic shell has better dispersibility in aqueous solution, biological and cell compatibility in organisms, it can be used as a controlled release carrier for substituting conventional drugs. Third, to graft bioactive sites on the surface of nanoparticles is very important for many biological applications. Many materials are difficult to bind a specific type of biomolecule, while the core-shell nanoparticles are advantageous for solving this problem. Fourth, when a core material is easily affected by thermal or chemical parameters in surrounding environments, the shell of inert material can facilitate to enhance the stability of the core material.

The core/shell nanoparticles are designed for biomedical applications based on the surface chemical properties of nanoparticles, which are the primary approaches for enhancing the affinity of nanoparticles with drugs, receptors, and ligands. The increased biocompatibility and cytocompatibility of nanomaterials provides a new approach for the medical applications of nanotechnology, for example, increasing the residence time of nanoparticles in the body, increasing the biomass transfer efficiency, reducing the administration dosage and frequency, and increasing the targeting of drugs, etc. A specific example is that a biomimetic polymer coating for a hydrophobic drug can promote controlled release of the drug at a target by environmental stimuli such as ion concentration, temperature, pH, etc. In addition, core/shell nanoparticles are also widely used in bioimaging applications due to their better biocompatibility compared to simple nanoparticles. Among the applications, bioimaging mainly relies on core materials, while shell materials can provide the surface performance such as biocompatibility and chelation with bioactive molecules. The thickness of the shell can be adjusted to provide sufficient contrast and ability to bind to target biomolecules, so as to achieve the functions of drug delivery, specific binding, and biosensing, etc.

US2008/0003292 discloses a process for preparing gelatin nanoparticles using a conventional reaction chamber. The nanoparticles have a maximum particle size of 350 nm, which can be used as a drug delivery system. According to the process disclosed, the gelatin particles are prepared by dropwise adding acetone to the gelatin aqueous solution, which is difficult to control and difficult to produce continuously.

CN103841965A discloses a continuous process for preparing gelatin nanoparticles in a process flow-chemistry reactor comprising a mixing unit, wherein the invention uses a millimeter-scale process flow-chemistry reactor, and water soluble gelatin solution and water soluble solvent are injected to the reactor at different flow rates. The particle size of gelatins prepared by this process is no more than 800 nm, which cannot be used for preparation of composite particles; the dimension of the flow channel was at millimeter-scale, and the mixing efficiency between aqueous phase and organic solvent was rather slow with a typical reaction time of more than 15 seconds.

WO2012051220A1 discloses a preparation technique of composite microspheres in which magnetic nanoparticles are coated with a biopolymer material, wherein the preparation of microspheres are required using an oil-in-oil emulsion method/solvent evaporation method, and emulsion is dispersed by applying a high energy shear force, the emulsion is also cleaned to obtain the final product. The process is complicated with a high cost.

In summary, the currently existing techniques for preparing core-shell composite nanoparticles are still limited by the following problems.

1) Existing preparation methods for gelatin nanoparticles are limited to the preparation of nanoparticles of simple organic phase, and single-phase gelatin nanoparticles have low mechanical strength and rather simple functions.

2) The existing technology for preparing composite microspheres is mainly based on the emulsion method, it needs to disperse two phases which cannot be blended (such as water and oil) into an emulsion by applying high energy shear force, followed by further cross-linking or polymerization to solidify the structure of the particles. This method involves the use of surfactants, additional cleaning steps, thus increases the cost, and it is difficult to completely remove the surfactants that normally used for preparing the emulsion, therefore limiting its applications.

3) The technology for preparing particles based on emulsion method is mostly used to prepare micron-sized particles, while the preparation of nanoparticles requires higher energy to break up droplets (such as ultra-high speed stirring or ultrasonic agitation) and more stable surfactants to reduce interface energy to form an emulsion of nano-sized droplets. The high-energy breaking techniques may destroy the chains of molecular materials and cannot be used for embedding of drugs or biologically active factors that are sensitive to external high-energy shear forces.

4) For preparation of the colloidal material systems that are composed of microparticles and have poor injectability, and the specific surface area of the microparticles is lower than that of the nanoparticles, thus there are fewer cross-linking points among the formed colloidal network. For another, the colloidal network composed of purely polymer-based particles normally shows poor mechanical strength, thereby restraining their applications in load-bearing conditions. Therefore, to enhance the mechanical properties of colloidal gels, it is important to prepare colloids with much higher stiffness. The design and preparation of core-shell structured microparticles with a rather stiff inorganic core and polymer shell can solve this problem by enhancing the mechanical strength of individual colloidal particles and providing polymeric shell that enables chemical functionalization and crosslinking between colloidal particles to form a stronger colloidal gel network.

SUMMARY OF THE INVENTION

In view of the defects of the prior art, the present invention provides a method for preparing inorganic nanoparticle-gelatin core-shell composite nanoparticles. By using inorganic nanoparticles as a core and gelatin as a shell layer, the composite nano-sized particles are prepared by a coprecipitation method. The method is simple and convenient, laying a foundation for the industrial mass production.

The present invention provides the following technical solutions:

A method for preparing inorganic nanoparticle-gelatin core-shell composite particles, comprising the following steps:

(1) dispersing inorganic nanoparticles uniformly in deionized water, maintaining the temperature of the solution at 30~60° C. for more than 30 min, then dissolving gelatin in the inorganic nanoparticle dispersion solution at 30~60° C. for at least 30 min to get a homogeneous gelation solution with inorganic nanoparticles evenly dispersed inside, thereafter adjusting the pH of the solution to either acidic 1-5 or basic 9-14, to obtain a gelatin aqueous solution with dispersed inorganic nanoparticles;

(2) dropwise adding polar organic solvent to the gelatin aqueous solution with dispersed inorganic/organic nanoparticles obtained in step (1), maintaining stirring during adding the organic solvent, to obtain a suspension of inorganic nanoparticle-gelatin core-shell composite micro/nano-particles;

(3) adding a cross-linking agent of gelatin polymer to the suspension containing the composite particles, maintaining the temperature at 30-60° C. and stirring at 500-1000 rpm to allow a cross-linking reaction lasting for 1~12 h; repeating centrifugation or ultrafiltration and re-suspending in deionized water to obtain inorganic nanoparticle-gelatin core-shell composite micro/nano-particles with the inorganic nanoparticle as the core and gelatin as the shell;

wherein, the composite material particles have an average diameter of 20 nm to 2 μm.

In some implementations, the gelatin concentration is 0.5 to 20 w/v % in the gelatin aqueous solution with dispersed inorganic nanoparticles in step (1), which is preferably 1 to 10 w/v %, and more preferably 2.5 to 5 w/v %.

In some implementations, the inorganic nanoparticle is at least one of lithium magnesium silicate nanoparticle (laponite), hydroxyapatite nanoparticle, calcium phosphate nanoparticles, graphene nanoparticle, black phosphorus nanosheet, carbon nanotube, iron oxide nanoparticle and barium titanate nanoparticle.

In some implementations, the mass ratio of the inorganic nanoparticles to the gelatin is 0.01 to 1 in the gelatin aqueous solution having dispersed inorganic nanoparticles obtained in step (1), which is preferably 0.05 to 0.7, more preferably 0.1 to 0.5.

In some implementations, in step (1), the pH of the solution is adjusted to acidic 1 to 5, preferably acidic 2 to 4; or the pH of the solution is adjusted to basic 9 to 12, preferably basic 10 to 11 by sodium hydroxide.

In some implementations, the polar organic solvent in step (2) is at least one of methanol, ethanol, isopropanol, butanol, acetone, acetonitrile or tetrahydrofuran. The volume of the polar organic solvent added is more than one time the volume of the gelatin aqueous solution with dispersed inorganic nanoparticles.

In some implementations, the cross-linking agent in step (3) is at least one of glutaraldehyde, glyceraldehyde, formaldehyde, carbodiimide, dihaloalkane, isocyanate, diisocyanate, transglutaminase and genipin.

In some implementations, in step (3), the molar ratio of the added cross-linking agent to the amine group in gelatin macromolecules is 0.25 to 10.0, preferably 0.5 to 1.0.

The present invention also provides a process for preparing inorganic nanoparticle-gelatin core-shell composite nano particles using a microfluidic chip device, comprising the following steps:

(1) preparing gelatin aqueous solution with dispersed inorganic nanoparticles according to the method described above;

(2) using the gelatin aqueous solution with dispersed inorganic nanoparticles as the disperse phase, using the polar organic solvent as the continuous phase, and the cross-linking agent as a third phase;

(3) injecting the disperse phase through the inlet of the disperse-phase fluid microchannel into the microfluidic chip at a first flow rate, and injecting the continuous phase through the inlet of the continuous-phase fluid microchannel into the microfluidic chip at a second flow rate, mixing the disperse phase and the continuous phase when they flows into a mixing channel, thereby obtaining a suspension of inorganic nanoparticle-gelatin core-shell composite nanoparticles;

(4) injecting the third phase at a third flow rate into a third phase fluid microchannel at the downstream of the microfluidic chip device, the third phase flows into the mixing channel and mixes with the suspension of the inorganic nanoparticle-gelatin core-shell composite nanoparticles in the mixing channel, being out of the chip through the output channel, the mixed solution is collected in a container;

(5) repeating centrifugation or ultrafiltration, and re-suspending the resultant composite particles collected in step (4), repeating this step with multiple times to obtain inorganic nanoparticle-gelatin core-shell composite nanoparticles composed of inorganic nanoparticle as the core and gelatin as the shell;

The composite particles have an average diameter of 20 nm to 2 μm.

In some implementations, the disperse phase fluid microchannel, the continuous phase fluid microchannel, the third phase fluid microchannel or the mixing channel has a cross-sectional area of $3 \times 10^{-5}$~5 mm², preferably $3 \times 10^{-4}$~5 mm², more preferably 0.3~3 mm².

In some implementations, the first flow rate, the second flow rate, and the third flow rate are 0.05~20 mL hr$^{-1}$, 0.1~100 mL hr$^{-1}$ and 0.05~2000 μL hr$^{-1}$, respectively.

In some implementations, the flow rate ratio of the second flow rate relative to the first flow rate is ranging from 1.0 to 10.0, preferably 2.0 to 3.5; and the flow rate ratio of the third flow rate relative to the first flow rate is 0.0067 to 0.067, preferably 0.0067 to 0.013.

In some implementations, after the disperse-phase and the continuous-phase being injected into the microfluidic chip through the corresponding microchannels, the disperse-phase liquid is rapidly mixed with the continuous-phase by forming laminar co-flow mode, or by forming flow-focusing mode depending on the geometry of the microfluidic channels.

The present invention also provides an injectable, self-healing inorganic/organic composite colloidal gel, the colloidal gel is obtained by blending lyophilized powders with an aqueous solution, lyophilized powders are the powders of inorganic nanoparticle-gelatin core-shell composite particles prepared according to the foregoing process described herein. Wherein, in the dispersion solution formed by blending the composite particles with the aqueous solution, the volume percentage of the composite particles is 5% to 150%, preferably 50% to 100%; the prepared colloidal gel has an elastic modulus of between 10 Pa to 200 kPa. The colloidal gel may also be obtained by directly blending the lyophilized powder with an aqueous solution with suspended cells or an aqueous solution with dissolved biologically active molecules. Wherein, the cell is selected from one of primary culture cell, subculture cell, culture cell of cell line and a heterozygote; the biologically active molecule is one of drug, protein, and signal factor. The colloidal gel can be used for the preparation of implantable filler material for tissue repair and regeneration.

The beneficial effects of the invention:

(1) The disclosure firstly provides a process for preparing core-shell composite nanoparticles with inorganic nanoparticle as the core and gelatin as the shell. The process is simple and convenient, having a high application value for industrial mass production.

(2) The prepared core-shell composite nanoparticles use the gelatin of good biocompatibility as shell layer, so the core-shell nanoparticles have good biocompatibility and cytocompatibility, and can be used as a controlled release carrier for delivery of biologically active protein drugs (for example, growth factors inducing tissue regeneration).

(3) The core-shell nanoparticles can be prepared by using different inorganic nanoparticles as the core. The preparation method is applicable to different core materials.

(4) The preparation method in the disclosure can be used to directly prepare core-shell nanoparticles through fluid reactor or microfluidic chip. The method enables continuous addition of the raw materials, and the reaction condition is more stable and more controllable, thus the parameters of the prepared products are more stable and controllable. Moreover, the production of the core-shell nanoparticles can be scaled-up by using of microfluidic chips that integrating a larger numbers of parallelized microchannels, to enhance the yield and rate of production, and facilitate the industrial production.

DETAILED DESCRIPTION OF THE EMBODIMENTS

The following non-limiting embodiments are provided to enable a person of ordinary skill in the art to fully understand the disclosure, but not to limit the disclosure in any way. In the following embodiments, unless otherwise stated, the experimental methods used are all conventional methods, and all materials and reagents used can be purchased from a biological or chemical company.

Embodiment 1

The hydroxyapatite-gelatin core-shell composite nanoparticles were prepared according to the following steps:

(1) hydroxyapatite nanoparticles prepared by hydrothermal synthesis was dispersed in 25 mL of deionized water to get a suspension with a concentration of hydroxyapatite at 0.005 g/mL, heated the nanoparticles suspension to 40° C., 1.25 g of gelatin was dissolved in it and maintained temperature at 40° C. continuously, the pH of the suspension was adjusted to 10 to get gelatin aqueous solution with dispersed hydroxyapatite nanoparticles, of which, the mixing ratio of hydroxyapatite to gelatin was 0.1:1 (w/w);

(2) 75 mL of ethanol was dropwise added to the obtained gelatin aqueous solution with dispersed hydroxyapatite nanoparticles with stirring continuously (1000 rpm) to obtain a suspension of core-shell composite nanoparticles with hydroxyapatite nanoparticles as the core and gelatin as the shell;

(3) 74 µL of 25% glutaraldehyde aqueous solution (cross-linking agent) was added to the suspension to crosslink the gelatin shell layer, the cross-linking reaction lasted for 12 hr. with continuous stirring at 1000 rpm at room temperature; then the resultant particles collected were repeatedly centrifuged (or ultrafiltrated) and washed to obtain hydroxyapatite-gelatin core-shell composite particles, of which, the centrifugation conditions were 5000 rpm, room temperature, centrifugation for 30 minutes to separate the particles and the supernatant;

(4) lyophilized powder of hydroxyapatite-gelatin core-shell composite particles were obtained by freeze drying.

Figure 1:
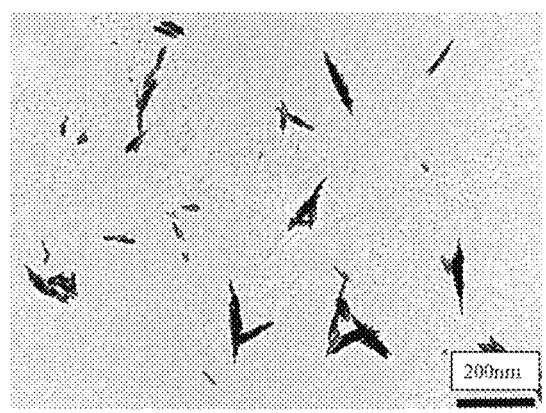
FIG. 1 is a TEM photograph of the hydroxyapatite nanoparticles used in Embodiment 1.
Figure 2:
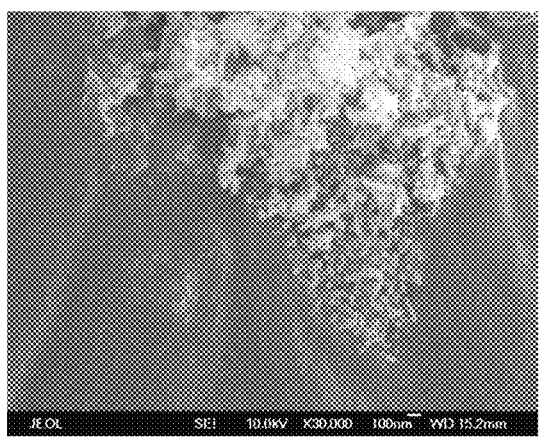
FIG. 2 is a SEM photograph of the hydroxyapatite nanoparticles used in Embodiment 1.

FIG. 1 and FIG. 2 are TEM photograph and SEM photograph of raw material needle-like hydroxyapatite nanoparticles respectively.

Figure 3:
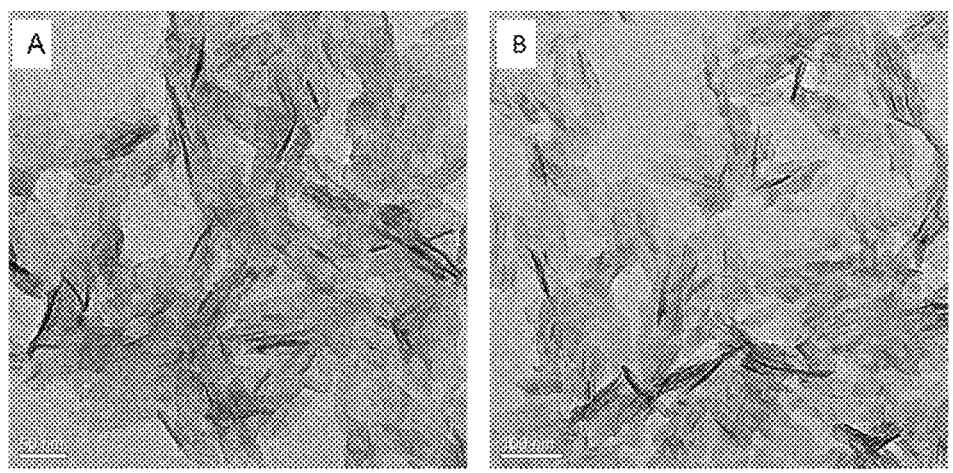
FIG. 3 is a TEM photograph of the hydroxyapatite-gelatin core-shell composite nanoparticles prepared in Embodiment 1.

FIG. 3 is a TEM photograph of the hydroxyapatite-gelatin core-shell composite nanoparticles prepared in Embodiment 1. As shown in the figure, the dark needle-like crystals are hydroxyapatite nanoparticles, while the gelatin is high polymer composition and low contrast, it shows light gray, surrounds the surface of the dark needle-like crystals. It confirms that the core-shell composite nanoparticles with hydroxyapatite as the core and gelatin as the shell have been successfully prepared according to the method in Embodiment 1.

Figure 4:
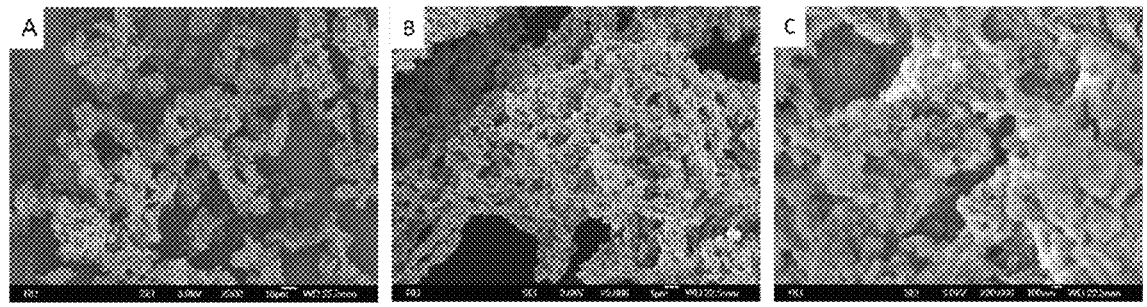
FIG. 4 is a SEM photograph of the hydroxyapatite-gelatin core-shell composite nanoparticles prepared in Embodiment 1.

FIG. 4 is a SEM photograph of the hydroxyapatite-gelatin core-shell composite nanoparticles prepared in Embodiment 1. It can be seen that the surface of the needle-like crystals is embedded by gelatin layer, confirming the composite nanoparticles having core-shell structure. FIG. 4A to 4C show SEM photographs at magnifications of 500, 5000, and 30000 respectively.

Figure 5:
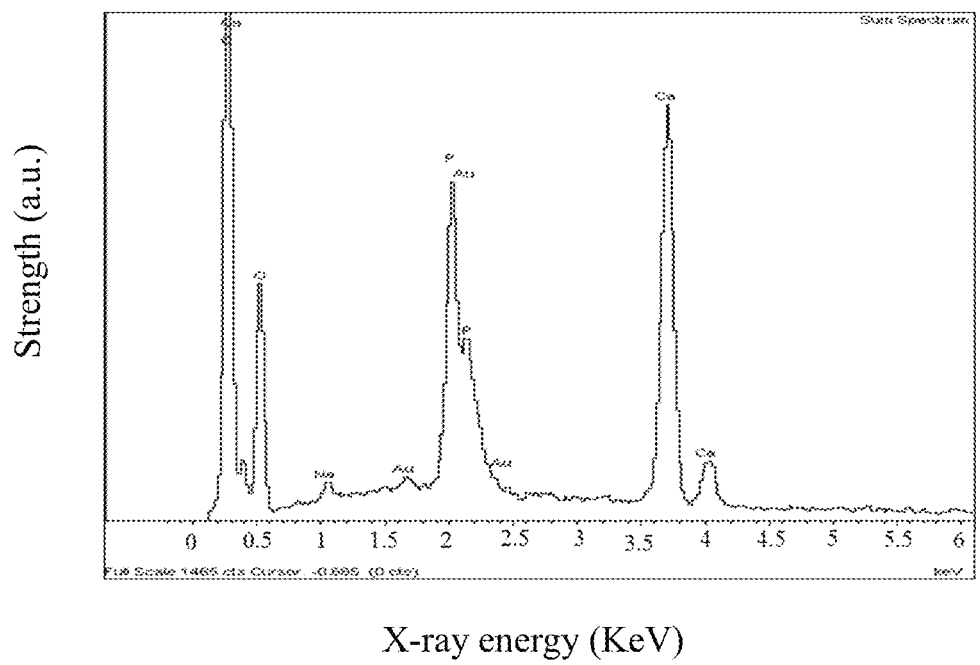
FIG. 5 is an x-ray elemental analysis of the hydroxyapatite-gelatin core-shell composite nanoparticles prepared in Embodiment 1.

FIG. 5 is an energy dispersive x-ray spectrometer analysis of the hydroxyapatite-gelatin core-shell composite nanoparticles prepared in Embodiment 1. It can be seen that the main element compositions of the composite nanoparticles include C, N, O, Ca and P, wherein C, N and O are the main elements of gelatin, and Ca and P are the main elements of hydroxyapatite, confirming that the components in the composite material are gelatin and hydroxyapatite.

Figure 6:
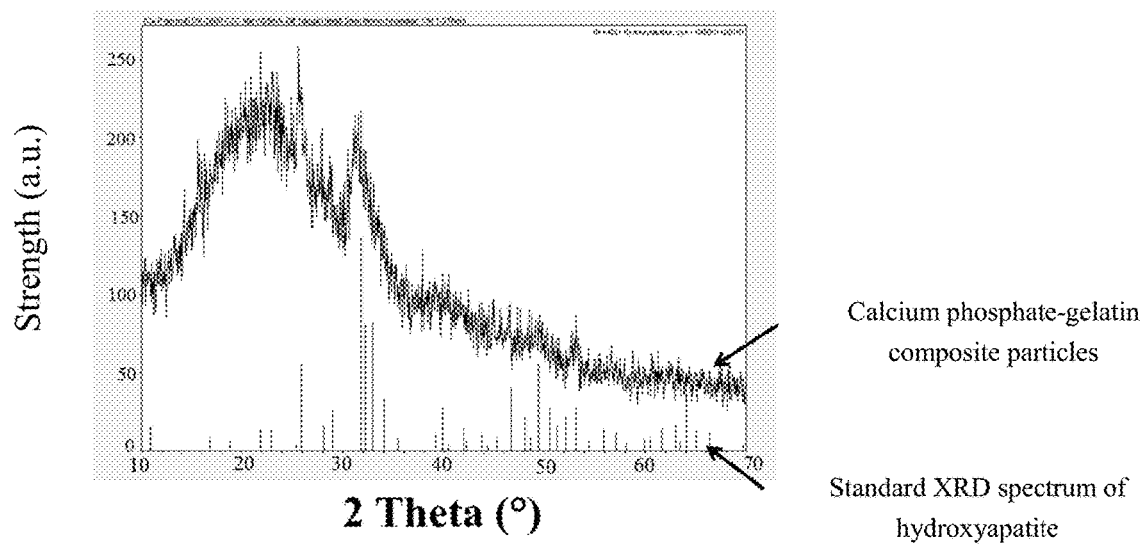
FIG. 6 is an x-ray diffraction spectrum of the hydroxyapatite-gelatin core-shell composite nanoparticles prepared in Embodiment 1.

FIG. 6 is an x-ray diffraction spectrum of the hydroxyapatite-gelatin core-shell composite nanoparticles prepared in Embodiment 1. Of which, the peaks at 2θ of 25.9° and 31.8° are the characteristic peaks of 002 crystal face and 211 crystal face of hydroxyapatite crystal, respectively, and the peaks at 20° are the diffraction peaks of gelatin. Since gelatin is an amorphous polymer, its diffraction peaks present dispersive peaks with a broad distribution. In FIG. 6, the diffraction spectra of crosslinked and uncrosslinked hydroxyapatite/gelatin composite nanoparticles show diffraction peaks of hydroxyapatite at 2θ=25.9° and 2θ=31.8°, and broad diffraction peaks of gelatin at 2θ=20°, reconfirming that the composite nanoparticles contain the components of hydroxyapatite and gelatin.

Figure 7:
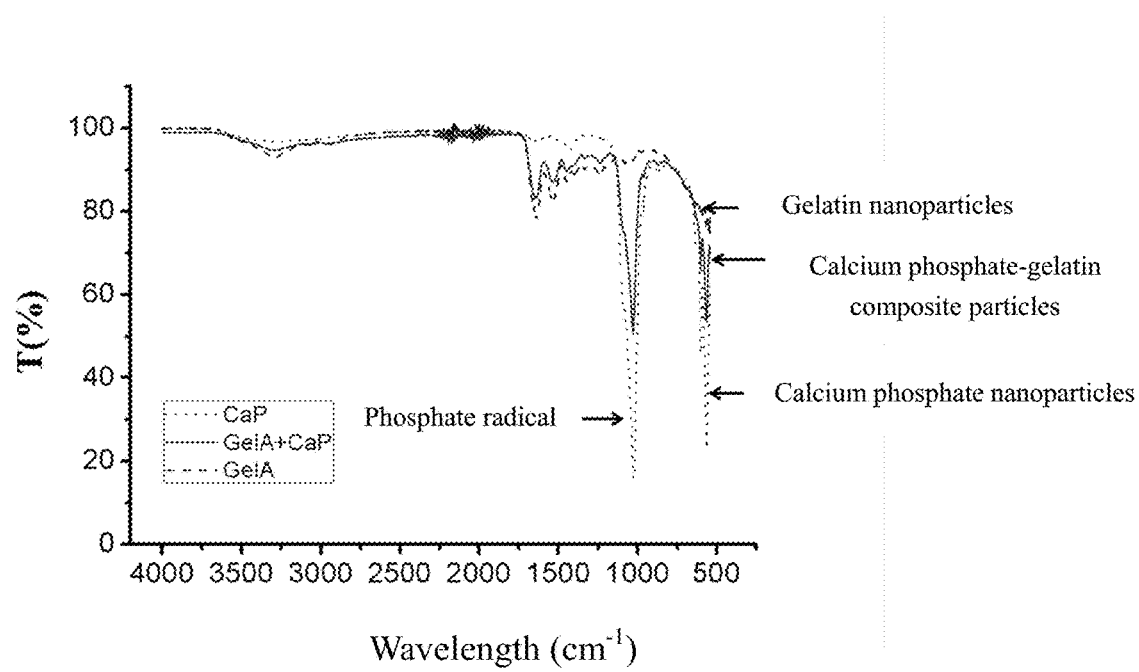
FIG. 7 is an infrared spectrum analysis of the hydroxyapatite-gelatin core-shell composite nanoparticles prepared in Embodiment 1.

FIG. 7 is an infrared spectrum analysis of the hydroxyapatite-gelatin core-shell composite nanoparticles prepared in Embodiment 1. In the figure, the peak at 3297 $cm^{-1}$ is the stretching vibration of the N—H bond of the amide bond in gelatin, the peak at 1631 $cm^{-1}$ is the stretching vibration of C=O in the amide bond, and the peak at 1527 $cm^{-1}$ is the bending vibration of N—H in the amide bond. The peaks of $PO_4^{3-}$ groups in pure hydroxyapatite nanoparticles at different positions are σ3-1(1090 $cm^{-1}$) and σ3-2(1040 $cm^{-1}$), respectively. These two characteristic peaks exist apparently in hydroxyapatite-gelatin composite nanoparticles, which reconfirming that composite particles contain the components of hydroxyapatite and gelatin.

The lyophilized powder of hydroxyapatite-gelatin composite colloidal particles prepared by the above method is blended respectively with different amounts of 10 mM NaCl aqueous solution and rapidly stirred to uniformly mix to obtain composite colloidal gel materials with different colloidal particle contents. The composite colloidal gel materials with different mass fractions can be obtained by changing the amount of the aqueous solution, and the viscoelastic properties of the obtained colloidal gel materials with different components are evaluated by rheometer. The results are shown in Table 1. As the mass fraction of composite colloids in the gel material increases, the storage (elastic) modulus of the gel material increases accordingly. When the mass fraction of colloidal particles is 25 wt. %, the hydroxyapatite-gelatin composite colloidal gel material has an elastic modulus of more than 120 kPa.

TABLE 1

Rheological storage (elastic) modulus G' of hydroxyapatite-gelatin composite colloidal gel materials with different mass fractions

| Mass fraction of composite colloidal particles (wt. %) | Storage (elastic) modulus G' (Pa) |
|---|---|
| 10 | 8329 ± 561 |
| 20 | 79055 ± 9803 |
| 25 | 121004 ± 13293 |

The self-healing behavior of colloidal gel is characterized by rheometer. The test method is as follows. Continuous rheological testing of the colloidal gels: firstly, an oscillating time sweep is performed under an oscillatory shear force of 1 Hz and a strain of 0.5%, to test the storage modulus (or elastic modulus, G') and the loss modulus (or viscous modulus, G") of the sample. In this case, the gel exhibits a rigidity of the solid under low shear force, as evidenced by the higher storage modulus G' value than the loss modulus G". The G' value at this stage is the initial elastic modulus of the sample, then the applied strain is gradually increased from 0.1% to 1000%. During the process, the colloidal gel sample is destroyed by applying an continuously increased shear force, which resulted into the gradual decrease of elastic modulus G', and finally crossing over with G"; this rheological response indicated that the colloidal gel changed from a rigid solid into a viscous flowable fluid-like material, as the colloidal network was destroyed. Then the shear force is removed immediately, and the recovery of elastic modulus was evaluated. After the shear force is released, the self-healing efficiency of gel is quantitatively assessed by the percentage of storage (elastic) modulus of sample recovery to its initial storage (elastic) modulus.

Figure 8:
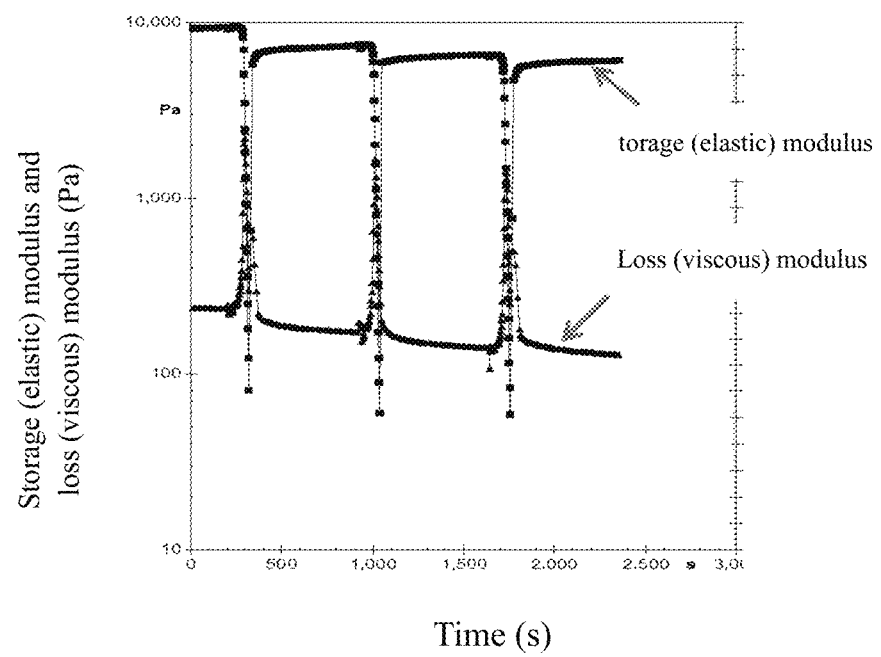
FIG. 8 is a rheological characterization of the self-healing behavior of the hydroxyapatite-gelatin composite colloidal gel prepared in Embodiment 1.

The self-healing efficiency of the hydroxyapatite-gelatin composite colloidal gel materials with different mass fractions of colloidal particles is shown in Table 2. Within 10 minutes after the composite colloidal gel materials are subjected to structural failure, the recovery ratio of the storage (elastic) modulus exceeds 60%. The self-healing process of the composite colloidal gel material is shown in FIG. 8. The elastic modulus of the gel material recovers instantaneously after shear failure, and the self-healing elastic modulus recovers more than 60% of the initial modulus within 10 minutes, and such self-healing behaviors can be repeated. Upon applying destructive shear forces for multiple cycles to the sample, followed by removal of the shear forces after the structural failure of the gels, a quick recovery of more than 60% of the initial elastic modulus of the gel is observed. These findings suggested the composite colloidal gels have remarkable self-healing capability.

TABLE 2

The self-healing efficiency of hydroxyapatite-gelatin composite colloidal gel materials with different mass fractions after shear failure

| Mass fraction of composite colloidal particles (wt. %) | Self-healing efficiency (%)* |
|---|---|
| 10 | 65 ± 9 |
| 20 | 71 ± 14 |
| 25 | 73 ± 11 |

*Note:
Self-healing efficiency is the percentage (%) of elastic modulus recovery detected within 10 minutes after the gel material is shorn by 1000% strain continuously for 60 s and the stress is released.

Comparative Example 1

Gelatin nanoparticles were prepared according to the following steps:

(1) 1.25 g of gelatin was dissolved in 25 mL of deionized water and maintained the temperature at 40° C. The pH of the aqueous solution was adjusted to 10 by dropwise adding NaOH solution to obtain an gelatin aqueous solution;

(2) 75 mL of anhydrous ethanol was dropwise added to the above gelatin aqueous solution, maintained the temperature at 40° C. with stirring at 1000 rpm, with the process of dropwise adding, a suspension of gelatin nanoparticle was formed; after the completion of addition, 74 μL of cross-linking agent glutaraldehyde (25 wt. % aqueous solution) was added to the above nanoparticle suspension to act a crosslinking reaction for 12 hr., then 100 mM glycine was added to the reaction product, to terminate the end groups of glutaraldehyde that had not been reacted completely;

(3) the resultant gelatin particles collected were repeatedly centrifugated (or ultrafiltrated) and re-suspended with multiple times to obtain gelatin nanoparticles, of which, the centrifugation conditions were 5000 rpm, room temperature, and centrifugation for 30 minutes to separate the particles and the supernatant;

(4) dry powder of gelatin nanoparticles were obtained by freeze drying the above gelatin nanoparticles suspension at −60° C.

Figure 9:
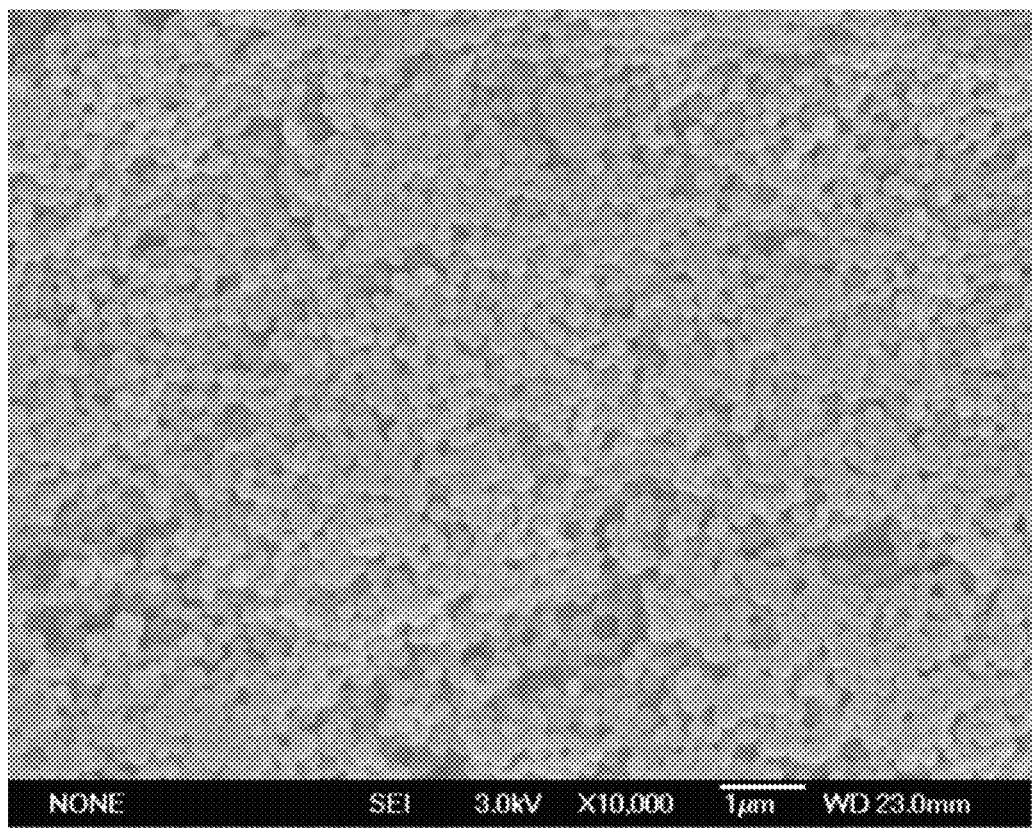
FIG. 9 is an SEM photograph of gelatin nanoparticles prepared in Comparative Example 1.

FIG. 9 is an SEM photograph of gelatin nanoparticles prepared in Comparative Example 1. It can be seen that the gelatin nanoparticles are spherical, and their particle sizes are 200 to 300 nm, which is completely different from that of hydroxyapatite-gelatin composite nanoparticles.

Figure 10:
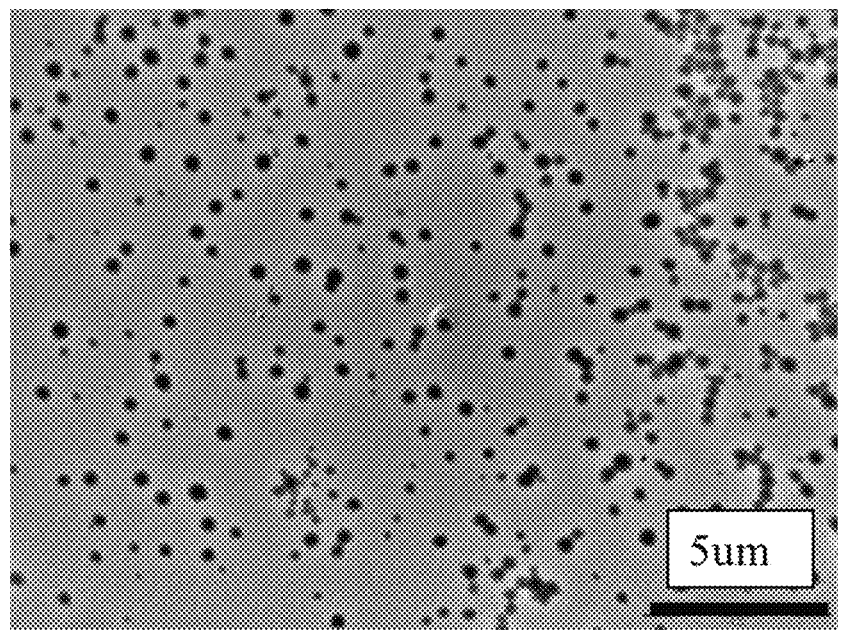
FIG. 10 is a TEM photograph of gelatin nanoparticles prepared in Comparative Example 1.
Figure 11:
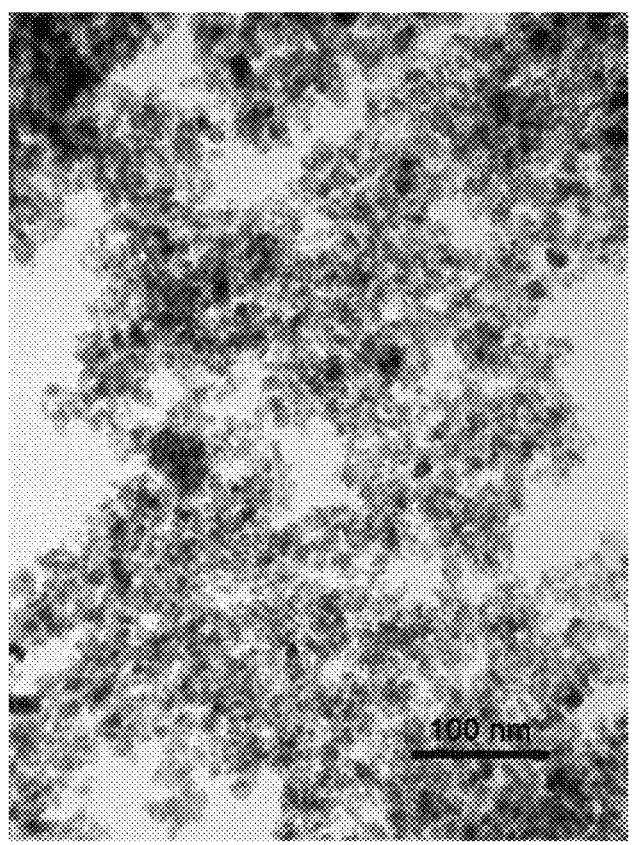
FIG. 11 is a TEM photograph of ferroferric oxide nanoparticles in Embodiment 4.
Figure 12:
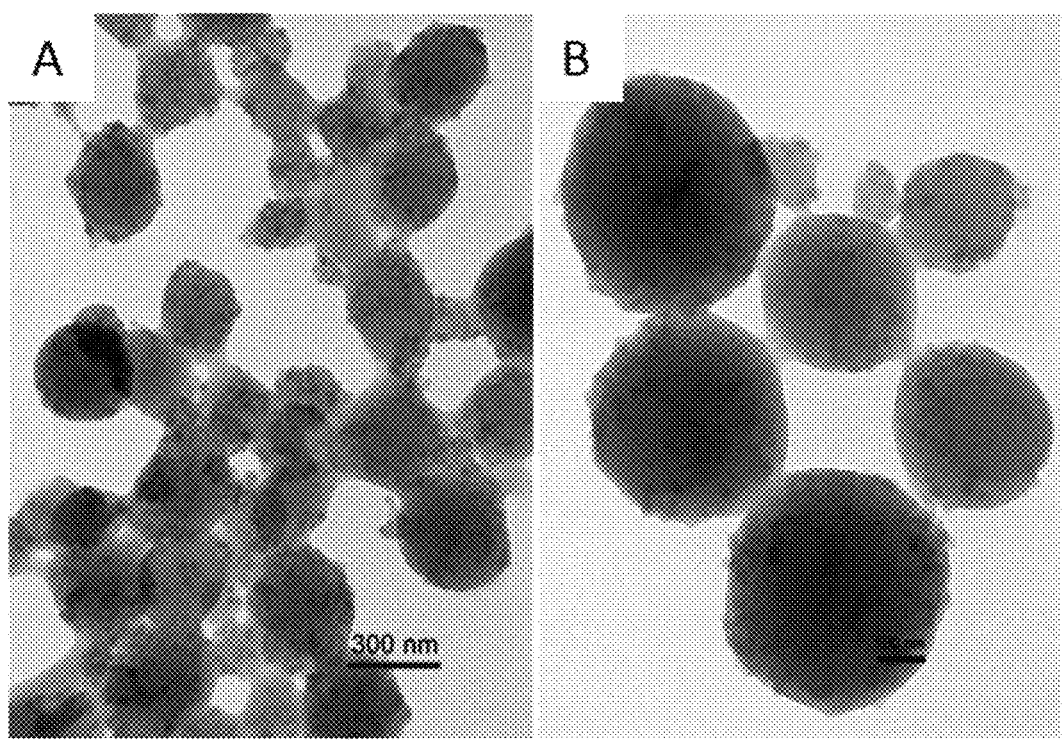
FIG. 12 is a TEM photograph of ferroferric oxide-gelatin core-shell composite nanoparticles prepared in Embodiment 4.

FIG. 10 is a TEM photograph of gelatin nanoparticles prepared by the method described in Comparative Embodiment 1. As shown from the figure, the gelatin nanoparticles are spherical, and the particle size of microspheres is in the range of 200 to 300 nm. The morphology is completely different from that of hydroxyapatite-gelatin composite nanoparticles.

Embodiment 2

Figure 14:
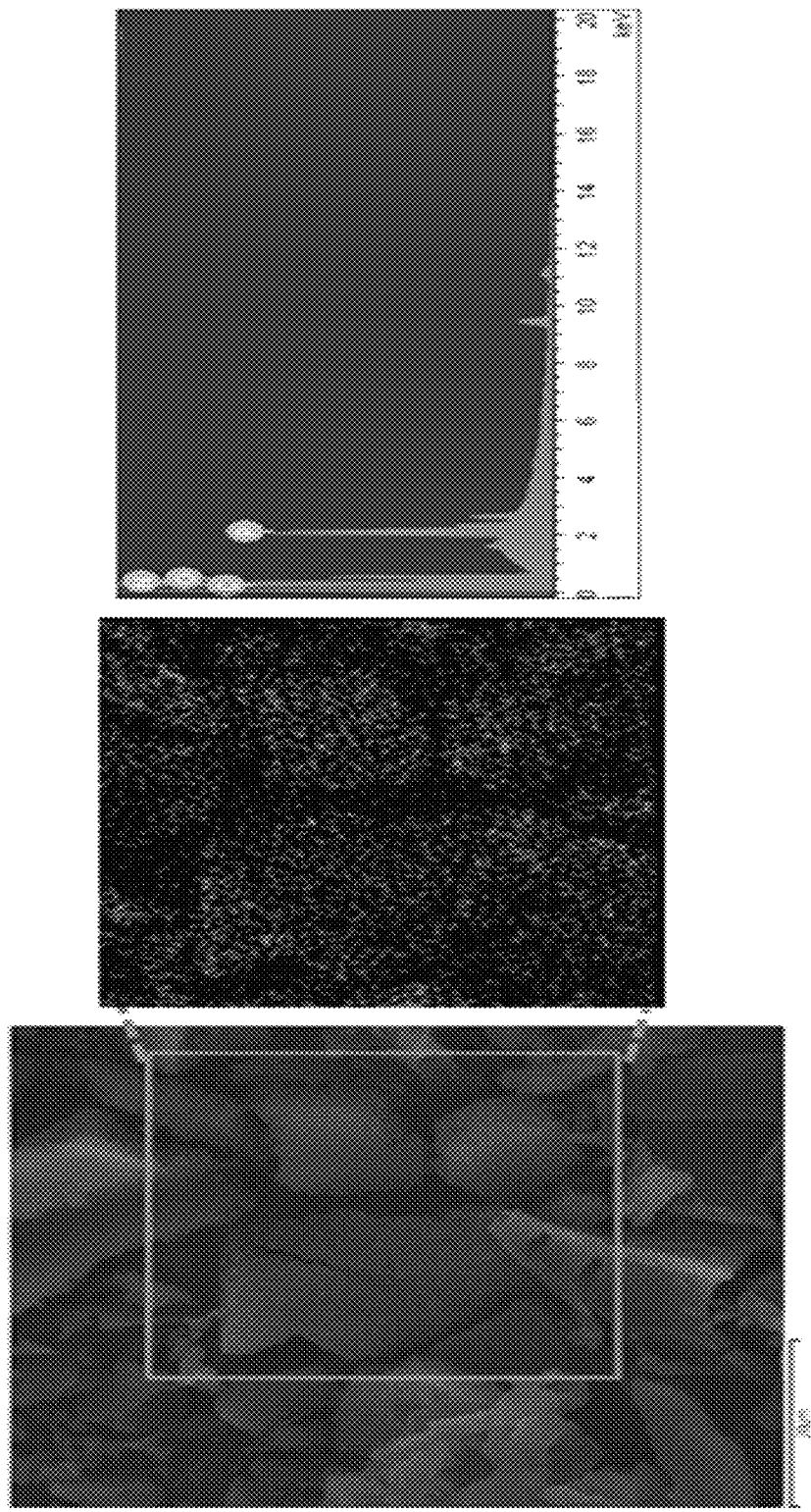
FIG. 14 is SEM and EDS photograph of black phosphorus nanosheet-gelatin core-shell composite nanoparticles prepared in Embodiment 3.

FIG. 14 is a TEM photograph of ferroferric oxide nanoparticles. It can be seen that the particle size of the ferroferric oxide nanoparticles is 50 to 80 nm and particles are in spherical shape.

Ferroferric oxide-gelatin core-shell composite nanoparticles were prepared using the above ferroferric oxide nanoparticles according to the following steps:

(1) ferroferric oxide nanoparticles were dispersed in 25 mL of deionized water to get a suspension with a concentration of ferroferric oxide at 0.01 g/mL, heated the nanoparticles suspension to 40° C. and 1.25 g of gelatin was dissolved in the nanoparticles suspension and maintained the temperature at 40° C., the pH of the solution was adjusted to 10 to get gelatin aqueous solution with dispersed ferroferric oxide nanoparticles, of which, the mixing ratio of ferroferric oxide to gelatin was 0.2:1 (w/w);

(2) 75 mL of acetone was dropwise added to the above gelatin aqueous solution with dispersed ferroferric oxide nanoparticles with stirring continuously (1000 rpm) to obtain a dispersion suspension of core-shell composite nanoparticles with ferroferric oxide as the core and gelatin as the shell;

(3) 74 μL of 25% glutaraldehyde aqueous solution (cross-linking agent) was added to the suspension to crosslink the gelatin shell layer, acting cross-linking reaction for 12 hrs with stirring at 1000 rpm at room temperature, then 100 ml of 100 mM aqueous solution of glycine was added to terminate the end groups of glutaraldehyde that had not been reacted completely; and then the resultant ferroferric oxide/gelatin particles collected were repeatedly centrifuged (or ultrafiltrated) and re-suspended to obtain ferroferric oxide/gelatin composite particles, of which, the centrifugation conditions were 5000 rpm, room temperature, and centrifugation for 30 minutes to separate the particles and the supernatant;

(4) lyophilized powder of ferroferric oxide-gelatin core-shell composite particles were obtained by freeze drying.

Figure 15:
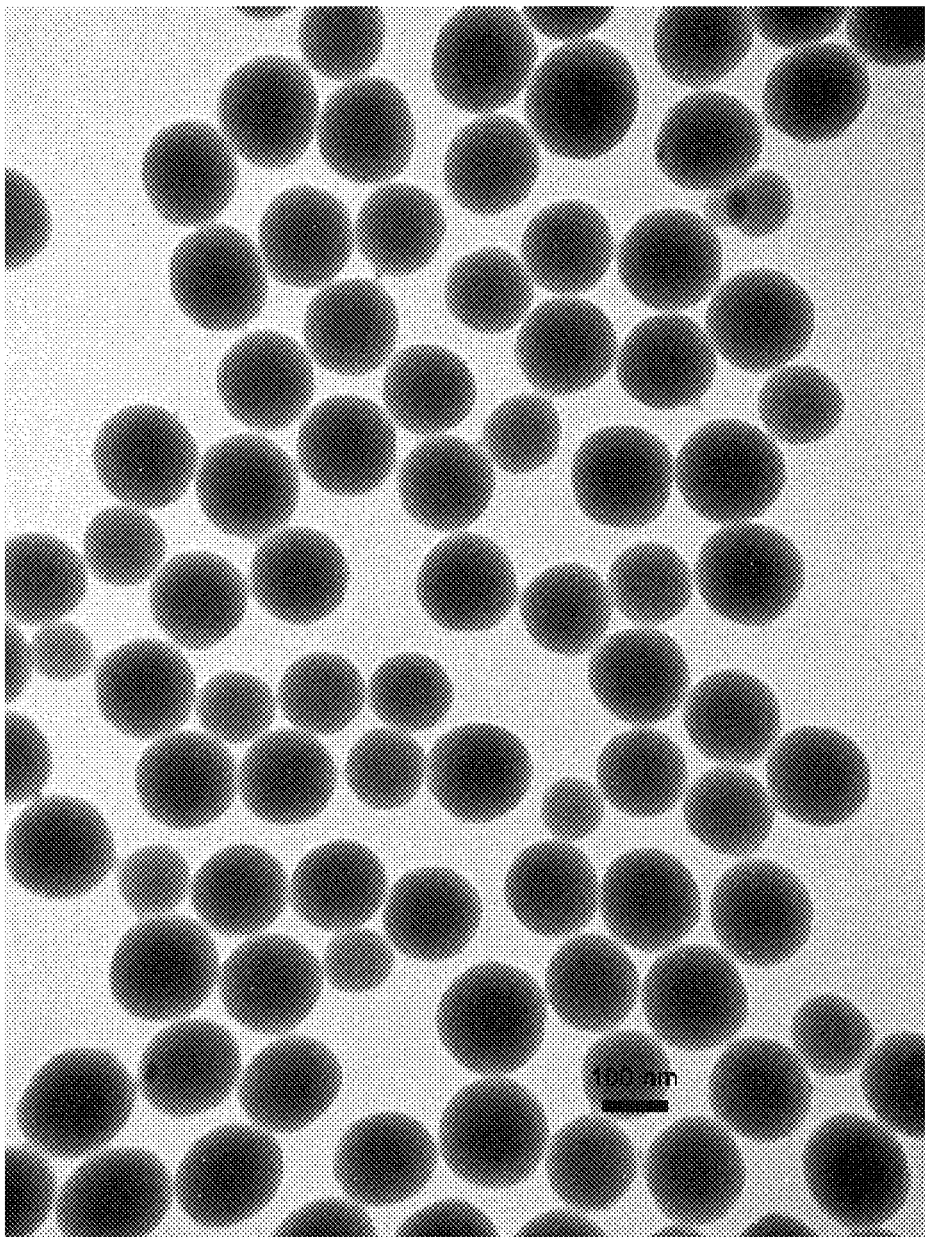
FIG. 15 is an TEM photograph of polystyrene nanoparticles used in Embodiment 4.

FIG. 15 is a TEM photograph of ferroferric oxide-gelatin core-shell composite nanoparticles prepared in Embodiment 2. As shown in FIG. 15, ferroferric oxide nanoparticles with a size of about 50 nm are embedded in gelatin microspheres.

Embodiment 3

Black phosphorus-gelatin core-shell composite nanoparticles were prepared according to the following steps:

(1) black phosphorus nanosheet was dispersed in 25 mL of deionized water to get a suspension with a concentration of black phosphorus nanosheet at 0.005 g/mL, heated the nanoparticles suspension to 40° C., 1.25 g of gelatin was dissolved in the nanoparticles suspension and maintained the temperature at 40° C., the pH of the solution was adjusted to 3 to get gelatin aqueous solution with dispersed black phosphorus nanosheet, of which, the mixing ratio of black phosphorus nanosheet to gelatin was 0.1:1 (w/w);

(2) 75 mL of acetone was dropwise added to the above gelatin aqueous solution with dispersed black phosphorus nanosheet with stirring continuously (1000 rpm) to obtain a dispersion suspension of core-shell composite nanoparticles with black phosphorus nanosheet as the core and gelatin as the shell;

(3) 74 μL of 25% glutaraldehyde aqueous solution (cross-linking agent) was added to the suspension to crosslink the gelatin shell layer, cross-linking reaction lasted for 12 hr. with stirring at 1000 rpm at room temperature, then 100 ml of 100 mM aqueous solution of glycine was added to terminate the end groups of glutaraldehyde that had not been reacted completely; and then the resultant black phosphorus/gelatin particles collected were repeatedly centrifuged (or ultrafiltrated) and re-suspended to obtain black phosphorus/gelatin composite particles, of which, the centrifugation conditions were 5000 rpm, room temperature, and centrifugation for 30 minutes to separate the particles and the supernatant;

(4) lyophilized powder of black phosphorus-gelatin core-shell composite particles were obtained by freeze drying.

Figure 13:
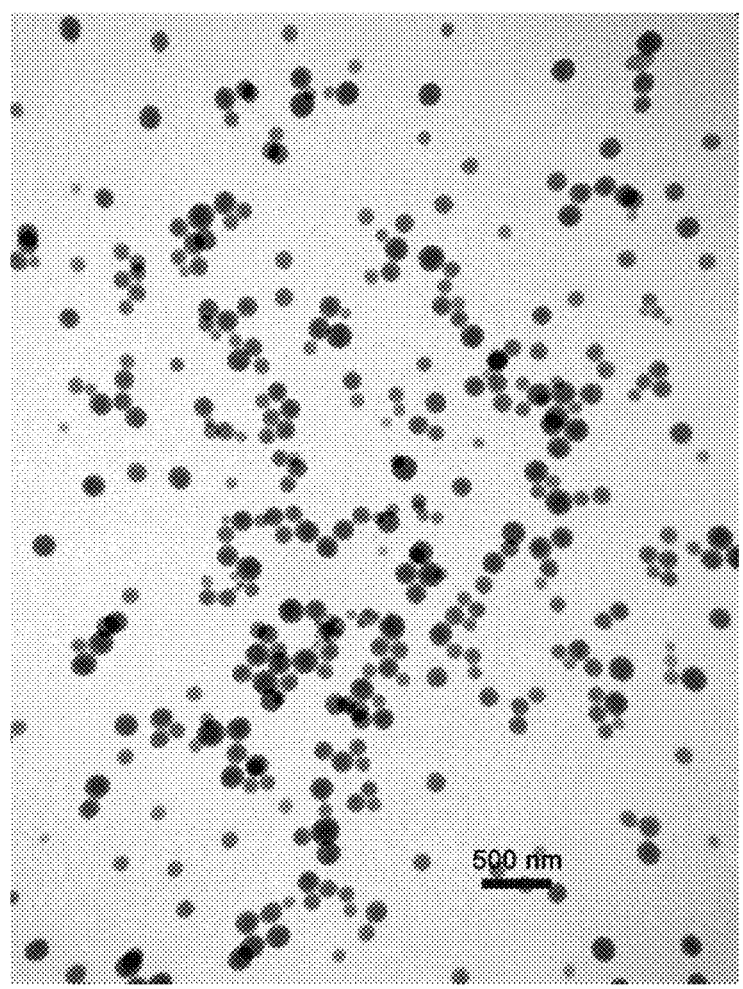
FIG. 13 is a TEM photograph of black phosphorus nanosheet-gelatin core-shell composite nanoparticles prepared in Embodiment 3.

FIG. 13 is a TEM photograph of black phosphorus nanosheet-gelatin core-shell composite nanoparticles prepared in Embodiment 3.

FIG. 14 is SEM and EDS photograph of black phosphorus nanosheet-gelatin core-shell composite nanoparticles prepared in Embodiment 3. It can be seen from the EDS figure that a large amount of phosphorus exists uniformly, confirming that the components in the composite material are gelatin and black phosphorus.

Embodiment 4

Polystyrene nanoparticles-gelatin core-shell composite nanoparticles were prepared according to the following steps:

(1) polystyrene nanoparticles were dispersed in 25 mL of deionized water to get a suspension with a concentration of Polystyrene nanoparticles at 0.005 g/mL, heated the nanoparticles suspension to 40° C., dissolved 1.25 g of gelatin in the nanoparticles suspension and maintained the temperature at 40° C., the pH of the solution was adjusted to 10 to get gelatin aqueous solution with dispersed Polystyrene nanoparticles, of which, the mixing ratio of Polystyrene nanoparticles to gelatin was 0.1:1 (w/w);

(2) 75 mL of ethanol was dropwise added to the above gelatin aqueous solution with dispersed Polystyrene nanoparticles with stirring continuously (1000 rpm) to obtain a dispersion suspension of core-shell composite nanoparticles with Polystyrene nanoparticles as the core and gelatin as the shell;

(3) 74 μL of 25% glutaraldehyde aqueous solution (cross-linking agent) was added to the suspension to crosslink the gelatin shell layer, cross-linking reaction lasted for 12 hr. with stirring at 1000 rpm at room temperature, then 100 ml of 100 mM aqueous solution of glycine was added to terminate the end groups of glutaraldehyde that had not been reacted completely; and then the resultant polystyrene/gelatin particles collected were repeatedly centrifuged (or ultrafiltrated) and re-suspended to obtain polystyrene/gelatin composite particles, of which, the centrifugation conditions were 5000 rpm, room temperature, and centrifugation for 30 minutes to separate the particles and the supernatant;

(4) lyophilized powder of polystyrene nanoparticles-gelatin core-shell composite particles were obtained by freeze drying.

FIG. 15 is an TEM photograph of polystyrene nanoparticles used in Embodiment 4. It can be seen that the polystyrene nanoparticles are finely dispersed, and their particle sizes are 90 to 120 nm.

Figure 16:
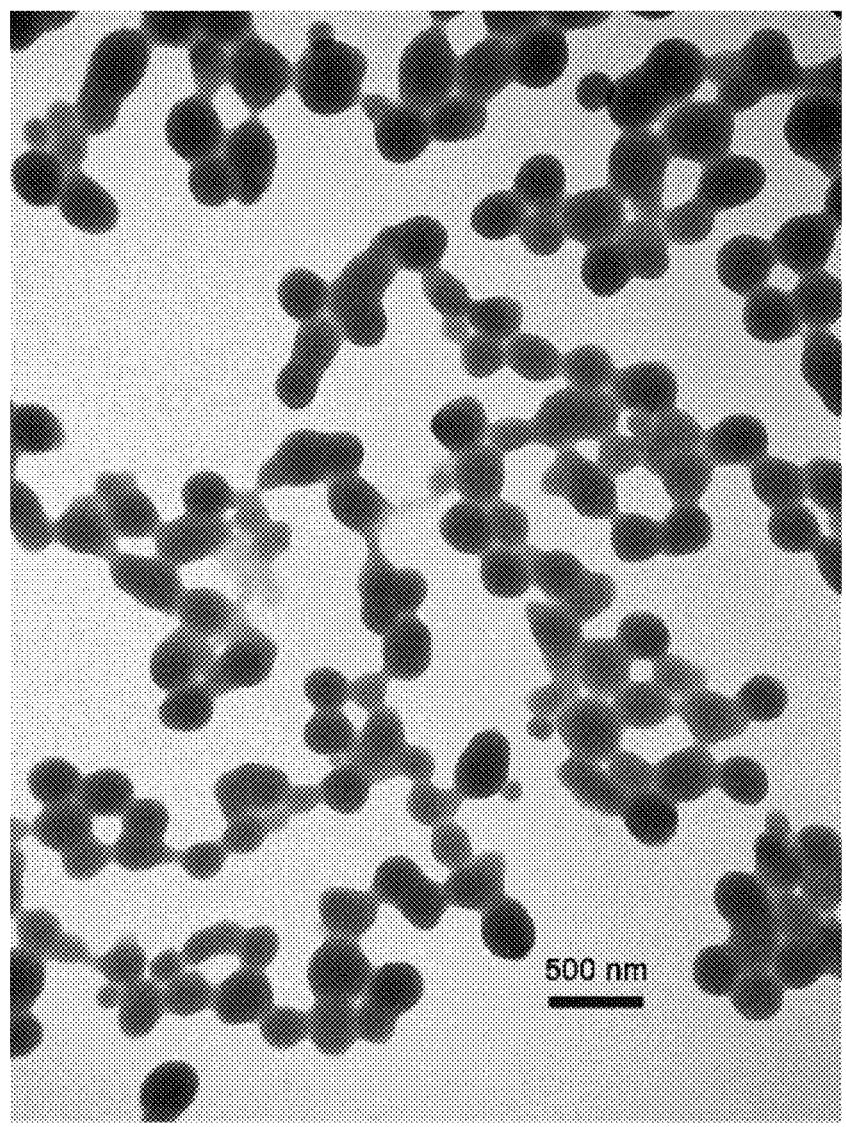
FIG. 16 is a TEM photograph of polystyrene nanoparticles-gelatin composite colloidal particles prepared in Embodiment 4.

FIG. 16 is a TEM photograph of polystyrene nanoparticles-gelatin composite colloidal particles prepared in Embodiment 4. As shown from the figure, the polystyrene nanoparticles are band together by the gelatin. The surface of the polystyrene nanoparticles is embedded by gelatin layer, confirming the composite nanoparticles having core-shell structure.

Embodiment 5

Figure 17:
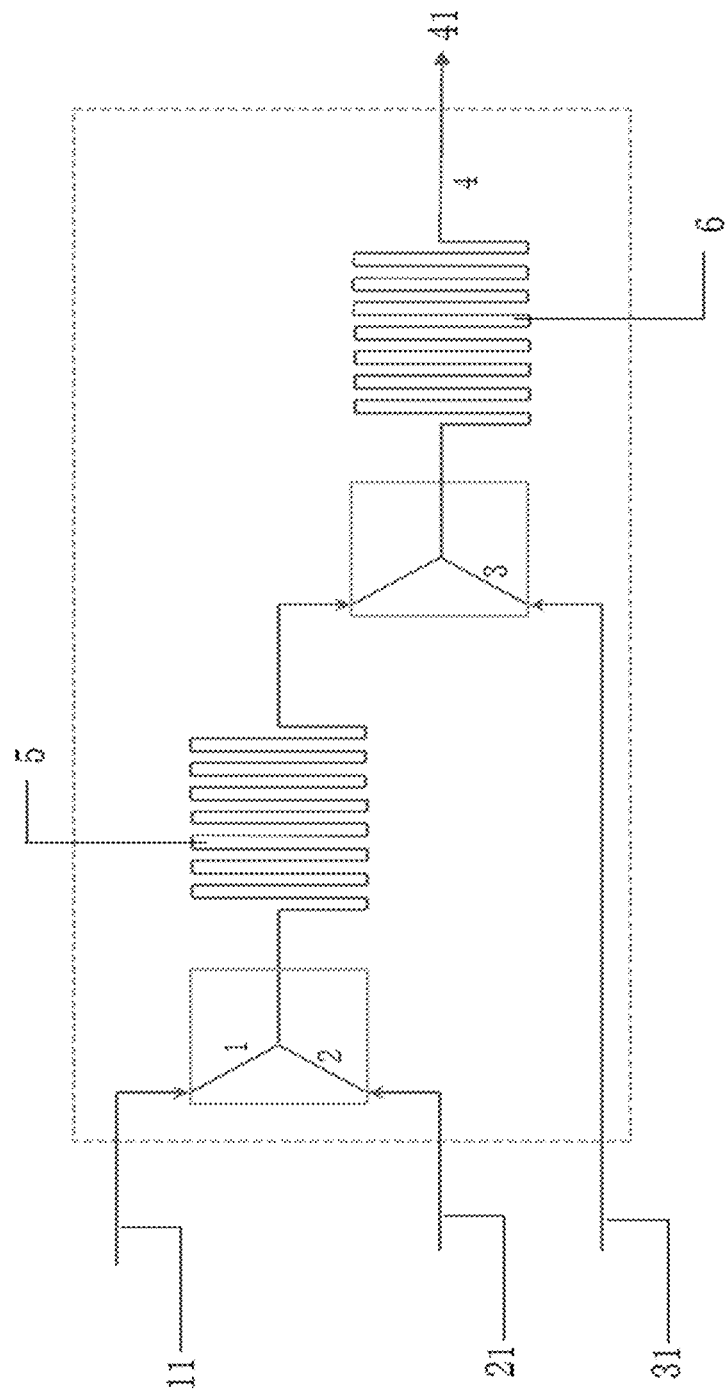
FIG. 17 is a fluid reaction chip device for preparing core-shell composite nanoparticles in Embodiment 7, wherein: 1—the first microchannel, 2—the second microchannel, 3—the third microchannel, 4—output channel, 5—U-type mixing channel I, 6—U-type mixing channel II, 11—inlet of the first microchannel, 21—inlet of the second microchannel, 31—inlet of the third microchannel, 41—outlet of the output channel.

The microfluidic reaction chip can adopt a conventional microfluidic chip device (reactor) as shown in FIG. 17. The preparation method includes the following steps:

(1) gelatin aqueous solution with dispersed hydroxyapatite nanoparticles, acetone solution and 25 wt. % aqueous solution of glutaraldehyde (cross-linking agent) were prepared according to the method described in Embodiment 1; the gelatin aqueous solution with dispersed hydroxyapatite nanoparticles was used as disperse phase, acetone solution as continuous phase, and cross-linking agent as the third phase;

(2) the disperse phase was injected from the inlet of the first microchannel into the first microchannel in the chip reactor, the continuous phase was injected from the inlet of the second microchannel into the second microchannel, and the two solutions blended in the U-shaped mixing channel I in the reactor to form turbid nanoparticles suspension;

(3) the third phase was injected from the inlet of the third microchannel into the third microchannel, and blended with the above suspension in the U-shaped mixing channel II to obtain a suspension of crosslinked hydroxyapatite-gelatin core-shell nanoparticles;

(4) the suspension was exported out of the chip through the outlet of the output channel and collected in the container with stirring, a 100 mM aqueous solution of glycine was added to the suspension to terminate the end groups of glutaraldehyde that had not been reacted completely;

(5) the nanoparticles suspension obtained in step (4) was repeatedly centrifuged (or ultrafiltrated) and re-suspended in deionized water to finally obtain a suspension of hydroxyapatite-gelatin core-shell composite nanoparticles in deionized water, and repeated the washing/re-suspending step for multiple times, of which the centrifugation conditions were 5000 rpm, room temperature, and centrifugation for 30 minutes to separate the particles and the supernatant;

(6) lyophilized powder of hydroxyapatite-gelatin core-shell nanoparticles were obtained by freeze drying the above suspension.

Wherein, the microfluidic reaction chip, each channel was a circular pipe with uniform diameter, and the cross section thereof was 1 mm$^2$. In step (2), the disperse phase injection speed was 1 mL/min, the continuous phase injection speed was 3 mL/min; and in step (3), the third phase injection speed was 0.013 mL/min.

In the above method, the channel of the microfluidic chip has a U-shaped mixing channel structure, and the fluids of disperse phase and continuous phase are blended in form of a laminar flow. A turbulent flow is gradually formed by the irregular collection structure of the channel, to achieve physical blending of the two phase fluids.

Embodiment 6

The microfluidic reaction chip may adopt a capillary microfluidic chip device as shown in FIG. 17, includes a disperse phase fluid microchannel, a continuous phase fluid microchannel, a cross-linking agent fluid microchannel, an output channel and a collection container. One end of the disperse phase fluid microchannel is unsealed inserted in one end of the continuous phase fluid microchannel, one end of the output channel is hermetically inserted in the other end of the continuous phase fluid microchannel, which is non end-to-end connected with the end of disperse phase fluid microchannel inserted into the continuous phase fluid microchannel. The cross-linking agent fluid microchannel is connected to the portion of output channel not inserted in the continuous phase fluid microchannel, and the other end (i.e. the outlet) of the output channel is connected to the collection container, the device can be fixed to a base for ease of use, and all channels are at the same horizontal level, the inner surface of each microchannel is subjected to a hydrophilic treatment.

The end of the disperse phase fluid microchannel inserted in the continuous phase fluid microchannel and the end of the output channel inserted in the continuous phase fluid microchannel are tapered; the disperse phase fluid microchannel, the continuous phase fluid microchannel and the cross-linking agent fluid microchannel are respectively connected to micro-peristaltic pump or micro-injector to achieve automatic sample injection; in the continuous phase fluid microchannel, the distance between the end of the disperse phase fluid microchannel to the end of the output channel is 200 μm. A portion of the output channel that is not inserted in the continuous phase fluid microchannel is provided with an exhaust port for discharging the gas in the chip when the fluid is injected into the chip.

Figure 18:
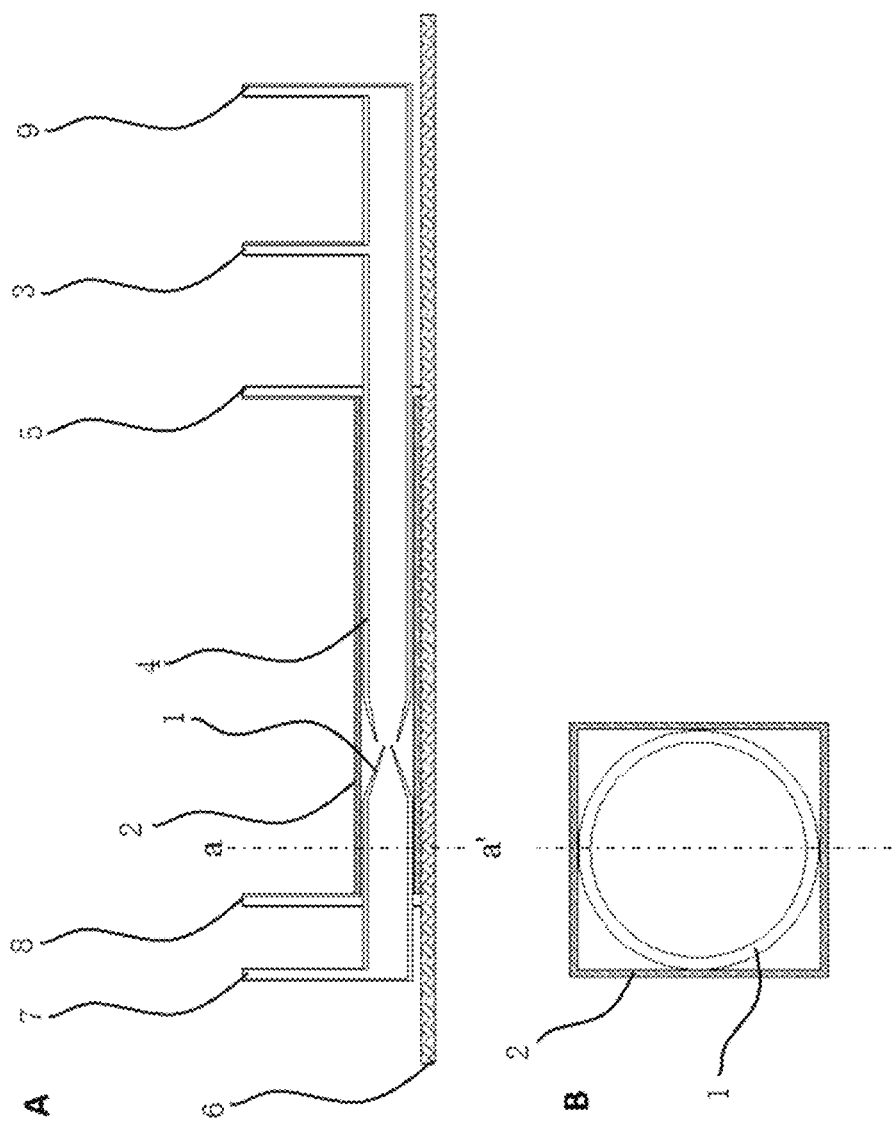
FIG. 18 is a schematic diagram of a capillary microfluidic chip device in Embodiment 8, wherein: 1—disperse phase fluid microchannel, 2—continuous phase fluid microchannel, 3—cross-linking agent microchannel, 4—output channel, 5—exhaust port, 6—base, 7—sample inlet of disperse phase fluid, 8—sample inlet of continuous phase fluid, 9—outlet of the output channel.

In the microfluidic chip device, the continuous phase fluid microchannel is a square glass capillary with a uniform inner diameter (inner diameter of 1.05 μm). The disperse phase fluid microchannel is a cylindrical AIT glass capillary with a uniform inner diameter (inner diameter of 560 μm), and the end inserted in the continuous phase fluid channel is a tapered end with an internal diameter of 30 μm. The output channel is a cylindrical AIT glass capillary with a uniform inner diameter (inner diameter of 560 μm), and the end inserted in the continuous phase fluid microchannel is a tapered end with an inner diameter of 60 μm. FIG. 18B is a cross-sectional view on the a-a' direction in FIG. 18A.

The preparation method includes the following steps:

(1) preparing gelatin aqueous solution with dispersed hydroxyapatite nanoparticles, acetone solution and 25 wt. % aqueous solution of glutaraldehyde (cross-linking agent) were prepared respectively according to the method described in Embodiment 1;

(2) the gelatin aqueous solution with dispersed hydroxyapatite nanoparticles were used as disperse phase, acetone solution as continuous phase, and cross-linking agent as the third phase;

(3) the disperse phase was injected to the disperse phase fluid microchannel from the sample inlet of disperse phase fluid and the continuous phase was injected to the continuous phase fluid microchannel from the sample inlet of continuous phase fluid respectively; the flow-focusing structure of the chip made the two phase solutions forming a concentric fluid in the chip, and blended by rapid material diffusion of the two-phase fluid in the microfluidic channel to form a turbid suspension of nanoparticles;

(4) the third phase was injected from the cross-linking agent microchannel disposed at the downstream of the output channel into the microfluidic chip device, and blended with the suspension formed in step (3) to obtain a suspension of crosslinked hydroxyapatite-gelatin core-shell nanoparticles.

(5) the suspension was exported from the chip through the outlet of output channel, and collected in the container and continuous stirring;

(6) 100 mM glycine was added to the suspension to terminate the end groups of glutaraldehyde that had not been reacted completely;

(7) the nanoparticles suspension obtained in step (4) was repeatedly centrifuged (or ultrafiltrated) and re-suspended in deionized water to finally obtain a suspension of hydroxyapatite-gelatin core-shell composite nanoparticles in deionized water, and repeated the washing/re-suspending step for multiple times, of which, the centrifugation conditions were 5000 rpm, room temperature, and centrifugation for 30 minutes to separate the particles and the supernatant;

(8) a lyophilized powder of hydroxyapatite-gelatin core-shell composite nanoparticles were obtained by freeze drying the above suspension.

In step (2), the disperse phase injection speed was 500 μL/hr., the continuous phase injection speed was 1.5 mL/hr.; and in step (3), the third phase injection speed was 6.5 μL/hr.

In the above method, the microfluidic chip device has a flow-focusing microchannel structure capable of forming a concentric fluid, the disperse phase and continuous phase form a flow-focusing flow stype, of which the disperse phase (aqueous solution) is mixed with the continuous phase (organic solvent). Thereby, the two phases can be mixed by rapid material diffusion between the two phases, thereby promoting rapid nucleation of the gelatin molecules at the surfaces of the hydroxyapatite nanoparticles, and gradually growing to form core-shell structure hydroxyapatite/gelatin composite nanoparticles.

The particle sizes of the hydroxyapatite-gelatin core-shell composite particles prepared by different methods in Embodiment 1, 5, and 6 were analyzed by laser particle analyzer, as shown in Table 3.

TABLE 3

Analysis of particle size of hydroxyapatite-gelatin core-shell composite particles prepared by different methods in different embodiments

| | Embodiment 1 (conventional process) | Embodiment 5 (U-shaped channel for mixing) | Embodiment 6 (flow-focusing channel for mixing) |
|---|---|---|---|
| Particle size (nm) | 234 ± 47 | 211 ± 18 | 228 ± 23 |

The results in Table 3 show that the hydroxyapatite-gelatin core-shell nanoparticles prepared by conventional process in Embodiment 1 have a particle size of 234±47 nm; and the hydroxyapatite-gelatin core-shell nanoparticles prepared by U-shaped mixed fluid reactor in Embodiment 5 have a similar particle size to those prepared by flow-focusing microfluidic chip in Embodiment 6, and have a narrow distribution of particle sizes.

The invention claimed is:

1. Method for preparing inorganic nanoparticle-gelatin core-shell composite particles, comprising the following steps:
   (1) dispersing inorganic nanoparticles uniformly in deionized water, maintaining the temperature of the solution at 30~60° C. for more than 30 min, then dissolving gelatin in the inorganic nanoparticle dispersion solution at 30~60° C. for at least 30 min to get a homogeneous gelation solution with inorganic nanoparticles evenly dispersed inside, thereafter adjusting the pH of this solution to either acidic 1-5 or basic 9~14, to obtain a gelatin aqueous solution with dispersed inorganic nanoparticles;
   (2) dropwise adding polar organic solvent to the gelatin aqueous solution with dispersed inorganic nanoparticles obtained in step (1), maintaining stirring during adding the organic solvent, to obtain a suspension of inorganic nanoparticle-gelatin core-shell composite micro/nano-particles;
   (3) adding a cross-linking agent of gelatin polymer to the suspension containing the composite particles, maintaining stirring to allow the cross-linking reaction lasting for 1~12 hr.; repeating centrifugation or ultrafiltration, and re-suspending in deionized water, to obtain inorganic nanoparticle-gelatin core-shell composite micro/nano-particles with the inorganic nanoparticle as core and gelatin as shell;
   wherein, the composite particles have an average diameter of 20 nm to 2 μm.

2. The method according to claim 1, wherein the gelatin concentration is 0.5 to 20 w/v % in the gelatin aqueous solution with dispersed inorganic nanoparticles in step (1).

3. The method according to claim 1, wherein the inorganic nanoparticle is at least one of lithium magnesium silicate nanoparticle, hydroxyapatite nanoparticle, calcium phosphate nanoparticles, graphene nanoparticle, black phosphorus nanosheet, carbon nanotube, iron oxide nanoparticle and barium titanate nanoparticle.

4. The method according to claim 1, wherein the mass ratio of the inorganic nanoparticles to the gelatin is 0.01 to 1 in the gelatin aqueous solution with dispersed inorganic nanoparticles obtained in step (1).

5. The method according to claim 1, wherein the polar organic solvent in step (2) is at least one of methanol, ethanol, isopropanol, butanol, acetone, acetonitrile or tetrahydrofuran; the volume of the polar organic solvent added is more than one time the volume of the gelatin aqueous solution with dispersed inorganic nanoparticles.

6. The method according to claim 1, wherein the cross-linking agent of gelatin polymer in step (3) is at least one of glutaraldehyde, glyceraldehyde, formaldehyde, carbodiimide, dihaloalkane, isocyanate, diisocyanate, transglutaminase and genipin.

7. The method according to claim 1, wherein in step (3), the molar ratio of the added cross-linking agent to the amine group in gelatin macromolecules is 0.25 to 10.0.

8. A method for preparing inorganic nanoparticle-gelatin core-shell composite particles using a microfluidic chip device, comprising the following steps:
   (1) preparing gelatin aqueous solution with dispersed inorganic nanoparticles according to the method in claim 1; and using the gelatin aqueous solution with dispersed inorganic nanoparticles as the disperse phase, using the polar organic solvent as the continuous phase, and the cross-linking agent as a third phase;
   (2) injecting the disperse phase through the inlet of the disperse-phase fluid microchannel into the microfluidic chip at a first flow rate, and injecting the continuous phase through the inlet of the continuous-phase fluid microchannel into the microfluidic chip at a second flow rate, mixing the disperse phase and the continuous phase when they flows into a mixing channel, thereby obtaining inorganic nanoparticle-gelatin core-shell composite particles;
   (3) injecting the third phase at a third flow rate into a third-phase fluid microchannel at the downstream of the microfluidic chip device, the third phase flows into the mixing channel and mixes with the suspension of the inorganic nanoparticle-gelatin core-shell composite particles in the mixing channel, thereby cross-link the gelatin phase of the composite particles, then after being out of the chip through the output channel, the mixed solution is collected in a container;
   (4) repeating centrifugation or ultrafiltration and re-suspending the resultant composite particles collected in step (3), repeating this step with multiple times to obtain inorganic nanoparticle-gelatin core-shell composite particles composed of inorganic nanoparticle as the core and gelatin as the shell;
   wherein, the composite particles have an average diameter of 20 nm to 2 μm.

9. The method according to claim 8, wherein the disperse-phase fluid microchannel, the continuous-phase fluid microchannel, the third-phase fluid microchannel or the mixing channel has a cross-sectional area of $3\times10^{-5}$~5 mm$^2$.

10. The method according to claim 8, wherein the first flow rate, the second flow rate, and the third flow rate are 0.05~20 mL hr$^{-1}$, 0.1~100 mL hr$^{-1}$ and 0.05~2000 μL hr$^{-1}$, respectively.

11. The method according to claim 8, wherein the flow ratio of the second flow rate relative to the first flow rate is ranging from 1.0 to 10.0.

12. The method according to claim 8, wherein after the disperse-phase and the continuous-phase being injected into the microfluidic chip through the corresponding microchannels, the disperse phase liquid is rapidly mixed with the continuous-phase liquid by forming laminar co-flow mode or by forming flow-focusing mode depending on the geometry of the microfluidic channels.

* * * * *